United States Patent [19]

Untereker et al.

[11] Patent Number: 5,395,310
[45] Date of Patent: Mar. 7, 1995

[54] IONTOPHORESIS ELECTRODE

[75] Inventors: Darrel F. Untereker, Cedar; Joseph B. Phipps, Plymouth; Patrick T. Cahalan, Champlin; Kenneth R. Brennen, Fridley, all of Minn.

[73] Assignee: Alza Corporation, Palo Alto, Calif.

[21] Appl. No.: 631,753

[22] Filed: Dec. 21, 1990

Related U.S. Application Data

[63] Continuation of Ser. No. 264,238, Oct. 28, 1988, abandoned.

[51] Int. Cl.$^6$ ............................................. A61N 1/30
[52] U.S. Cl. ................................. 604/20; 607/152; 424/449
[58] Field of Search ............... 604/20, 890.1; 128/783, 128/798, 802; 424/447, 448, 449; 607/152

[56] References Cited

U.S. PATENT DOCUMENTS

| | | | |
|---|---|---|---|
| 4,051,002 | 9/1977 | Gunjima et al. | 204/98 |
| 4,250,878 | 2/1981 | Jacobsen et al. | |
| 4,383,529 | 5/1983 | Webster | 604/20 |
| 4,416,274 | 11/1983 | Jacobsen et al. | 604/20 |
| 4,519,973 | 5/1985 | Cahalan et al. | 264/267 |
| 4,585,652 | 4/1986 | Miller et al. | 424/449 |
| 4,640,689 | 2/1987 | Sibalis | 604/20 |
| 4,720,334 | 1/1988 | DuBois et al. | 204/98 |
| 4,722,726 | 2/1988 | Sanderson et al. | 604/20 |
| 4,731,049 | 3/1988 | Parsi | 604/20 |
| 4,744,787 | 5/1988 | Phipps et al. | 604/20 |
| 4,747,819 | 5/1988 | Phipps et al. | 604/20 |
| 4,752,285 | 6/1988 | Petelenz et al. | 604/20 |
| 4,756,710 | 7/1988 | Bondi et al. | 424/449 |

FOREIGN PATENT DOCUMENTS

| | | | |
|---|---|---|---|
| 203270 | 10/1985 | Japan | 604/20 |
| WO8704936 | 8/1987 | WIPO | |

OTHER PUBLICATIONS

Article entitled "Noninvasive Delivery of a Novel Inotropic Catecholamine: Iontophoretic Versus Intravenous Infusion in Dogs", by John E. Sanderson et al., published in the *Journal of Pharmaceutical Sciences*, vol. 76, No. 3, Mar. 1987, pp. 215–218.

Article entitled "Acrylic Ion-Transfer Polymers", by Ballestrasse 35 al., published in the *Journal of the Electrochemical Society*, Nov. 1987, vol. 134, No. 11, pp. 2745–2749.

Reference entitled "Principles of Polymer Systems", by F. Rodriquez, McGraw-Hill Book Co., 1979, pp. 382–390.

*Primary Examiner*—Ralph A. Lewis
*Attorney, Agent, or Firm*—Vidas, Arrett & Steinkraus

[57] ABSTRACT

An improved iontophoresis electrode employing a current distributing member and a drug reservoir containing an ionic drug. The drug reservoir is applied to the skin of a patient, and includes a charge selective ion permeable membrane adapted to contact the skin, through which the ionic drug is delivered.

8 Claims, 1 Drawing Sheet

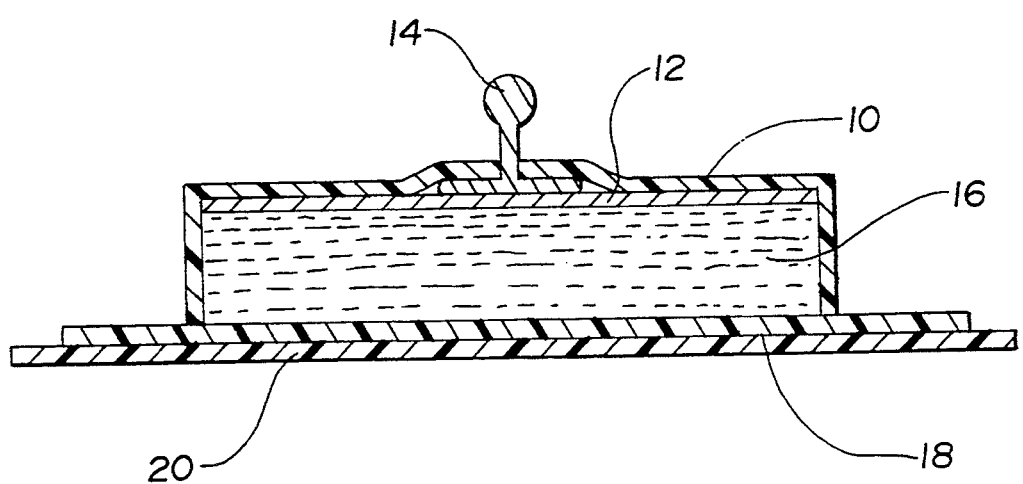

IONTOPHORESIS ELECTRODE

This is a continuation of application(s) Ser. No. 07/264,238, filed on Oct. 28, 1988, and now abandoned.

Reference is made to concurrently filed, commonly assigned U.S. patent application entitled "IONTOPHORESIS", ELECTRODE Ser. No. 264,239, filed Dec. 21, 1990 now U.S. Pat. No. 5,057,072 by Phipps, filed as of the date of this application. This application is hereby incorporated by reference in its entirety, Reference is also made to previously filed, commonly assigned U.S. patent application entitled "IONTOPHORETIC DRUG DELIVERY", Ser. No. 154,566, filed Feb. 10, 1988 by Untereker et al.

BACKGROUND OF THE INVENTION

This invention relates to methods and apparatus for transdermal medicament delivery and to improvements therein. More specifically, this invention relates to improved methods and apparatus for active (as opposed to passive) transdermal, ambulatory drug delivery. Yet more particularly, this invention relates to increasing the efficiency of iontophoresis devices and to improved methods of making and using such devices.

Recently, there has been a renewed interest in the technology of iontophoresis. Iontophoresis has been found to be useful in the transdermal administration or introduction of lidocaine hydrochloride, hydrocortisone, acetic acid, flouride, penicillin, dexamethasone sodium phosphate, and many other drugs. Perhaps the widest use of iontophoresis is the diagnosis of cystic fibrosis using pilocarpine nitrate iontophoresis.

In presently known iontophoresis devices, at least two electrodes are used. Both these electrodes are disposed so as to be in intimate electrical contact with some portion of the skin. The "active" electrode is the electrode from which the ionic drug is delivered into the body. The "indifferent" or ground electrode serves to close the electrical circuit through the body. A battery or other current source is coupled to the electrode to provide the electrical force to drive the drug into the body. For example, if the ionic substance to be driven into the body is positively charged, then the positive electrode (the anode) will be the active electrode and the negative electrode (the cathode) will serve to complete the circuit. If the ionic substance to be delivered is negatively charged, then the negative electrode will be the active electrode and the positive electrode will be the indifferent electrode. Of course, simultaneous delivery of drugs from both of the electrodes is also possible.

Generally, iontophoresis electrodes include a reservoir of the drug, typically compounded as a salt of the drug, for example a flouride or sulfate. These reservoirs may take the form of preformed gel bodies, such as disclosed in U.S. Pat. No. 4,382,529 issued to Webster, solid adhesive bodies as disclosed in U.S. Pat. No. 4,416,274, issued to Jacobson, or fluid reservoirs as disclosed in U.S. Pat. No. 4,250,878, issued to Jacobsen. Electrical current is typically applied to the fluid reservoir by means of a current distributing member, which may take the form of a metal plate, a foil layer, a conductive screen, or a dispersion of conductive particles within the drug reservoir.

Typically, the current distributing member in iontophoresis electrodes has been constructed of an inert material, such as stainless steel or platinum. However, more recently use of sacrificial current distributing members which are oxidized or reduced themselves during delivery of the drug has been discussed. Use of sacrificial current distributing members can avoid the pH changes and other adverse effects associated with the hydrolysis of water which generally accompanies the use of inert current distributing members. Electrodes with sacrificial current distributing members are disclosed in U.S. Pat. No. 4,744,787, issued to Phipps et al, incorporated herein by reference in its entirety. Such electrodes are also discussed in the above-cited copending application by Untereker et al, also incorporated herein by reference in its entirety.

An alternative approach to avoiding the adverse effects associated with hydrolysis of water at the current distributing member is disclosed in the published PCT Patent Application No. WO 87/04936, published Aug. 27, 1987, by Sanderson et al, corresponding to U.S. Pat. No. 4,722,726. This electrode system is also described in the article "Noninvasive Delivery of a Novel Inotropic Catecholamine: Iontophoretic Versus Intravenous Infusion in Dogs" by Sanderson et al, published in the *Journal of Pharmaceutical Sciences*, Vol. 76, No. 3, March 1987, pp. 215–218. In this electrode system, an inert current distributing member is used and the electrode is divided into an upper chamber filled with a buffer and a lower chamber containing the ionic drug. The upper chamber is separated from the lower chamber by means of an ion selective membrane. As described, it is apparently intended that the buffer solution in the upper chamber mitigate the effects of hydrolysis of water, and that the ion selective membrane isolate the drug from the contents of the upper chamber.

In electrodes including fluid reservoirs, as disclosed in U.S. Pat. No. 4,250,878 issued Jacobson, delivery of the drug typically takes place through a microporous membrane. Typically, such membranes are permeable based on size, and therefore must be permeable to any ion equal to or smaller than the drug ion intended to be delivered. In U.S. Pat. No. 4,640,689, issued on Feb. 3, 1987 to Sibalis, an iontophoresis electrode including a gel type drug reservoir provided with a semipermeable membrane is disclosed. This reference also suggests the use of an "ion selective retention gel" intermediate the drug reservoir and the semipermeable membrane. The ion to be retained by the gel is not discussed.

SUMMARY OF THE INVENTION

Typical iontophoresis electrodes must be permeable to the drug which they deliver. Generally, this has resulted in the electrode also being permeable to molecular species of equal or smaller size. During delivery of the drug, therefore, it is to be expected that ions of charge opposite to that of the drug to be delivered will migrate into the electrode. For example, in an electrode which delivers propranolol, compounded in the reservoir in the form of propranolol hydrochloride, a positive drug ion will be delivered. Because the electrode will be applied to the skin, it is to be expected that sodium chloride will be available at the electrode/skin interface, either from the tissues of the body or contained in sweat. Thus, as the positively charged propranolol ion migrates out of the electrode under the influence of the electrical field, chlorine ions present at the skin migrate into the electrode and provide an alternate ionic conductor. Because of the relatively smaller size of the chlorine ion, it migrates more readily under the influence of the electrical field than the typically larger drug ions. It is believed that this process dramatically reduces the efficiency of most iontophoresis electrodes.

The present invention provides a charge selective ion premeable membrane which is preferentially permeable to ions having the same charge as the drug ion. This membrane reduces transport of oppositely charged ions across the electrode/skin interface. The effect of sodium, chloride or other ions present in the skin which would otherwise provide an alternative ionic current path is thus minimized. By reducing the availability of other mobile charge carriers in the drug reservoir, efficiency of delivery of the ionic drug is increased.

This electrode structure is particularly beneficial in the context of an electrode employing a sacrificial current distributing member, as discussed above. By providing a current distributing member which is oxidized or reduced at a voltage less than that of water (e.g. silver or silver/silver chloride) in conjunction with a current limited power source, electrolysis of water is reduced or eliminated. This is discussed in more detail in U.S. patent application Ser. No. 154,566, for "IONTOPHORETIC DRUG DELIVERY" filed Feb. 10, 1988 by Untereker et al, incorporated herein by reference in its entirety. Such sacrificial current distributing members are also disclosed in U.S. Pat. No. 4,744,787 issued to Phipps et al, and also incorporated herein by reference in its entirety.

Eliminating hydrolysis in the electrode prevents formation of charged species ($OH^-$ and $H_3O^+$) within the electrodes. This further reduces the availability of ionic current carriers other than the drug ions. Thus, the combination of the sacrificial current distributing member with the charge selective ion permeable membrane provides a particularly advantageous iontophoresis electrode.

BRIEF DESCRIPTION OF THE DRAWING

FIG. 1 shows a cross sectional view of an iontophoresis electrode embodying the present invention.

DETAILED DESCRIPTION OF THE INVENTION

FIG. 1 shows a sectional view through an iontophoresis electrode according to the present invention. The electrode is mounted within a non-conductive housing 10, which contains a current distributing member 12, here illustrated as a metallic foil or plate. Current distributing member 12 may also take the form of a screen or a dispersion of conductive particles within the drug reservoir 16. Reservoir 16 contains the drug to be delivered. Current distributing member 12 is preferably a sacrificial current distributing member. Alternatively, member 12 may be fabricated of an inert metal such as platinum or stainless steel.

In one embodiment of the invention, current distributing member 12 takes the form of a sacrificial current distributing member, which is readily oxidized or reduced. If the drug ion to be delivered is positively charged, the electrode (anode) would include a current distributing member 12 made of a readily oxidizable metal, such as silver, and the drug would be compounded with a counterion which forms a neutrally charged and preferably insoluble compound when reacted with ionic silver. One example would be lithium chloride. As the silver in the current distributing member is oxidized, it will react with the chlorine ions within the reservoir 16 to form a silver chloride precipitate. The positive lithium ions will be free to migrate through the reservoir 16.

If the drug ion to be delivered is negatively charged, the electrode (cathode) would include a current distributing member 12 made of readily reducible material, such as silver/silver chloride, and the drug would be compounded with a counterion which forms a neutrally charged and preferably insoluble compound when reacted with chloride ion, for example, silver or copper salicylate. As ionic silver in the silver chloride portion of member 12 is reduced, the released chlorine ions will react with the silver or copper counterions compounded with the drug to form insoluble silver chloride. The negative salicylate ions will be free to migrate through the reservoir 16.

Current distributing member 12 is coupled to a snap connector 14, which facilitates connection of the electrode to a source of electrical current. Typically, such power sources used with the electrode will be current limited, so that the electrical potential at the electrode will be established by the chemistry of the electrode itself.

Drug reservoir 16 contains the ionic drug to be delivered. Examples of cationic drugs deliverable by iontophoresis include lithium and pilocarpine. Examples of anionic drugs appropriate for delivery by iontophoresis include salicylate and flouride. Preferably, this reservoir takes the form of a gel, but may take the form of a liquid. Preferably, drug reservoir 16 is free of ionic or readily ionizable material other than the drug to be delivered. For example, the matrix may take the form of a polar, nonionic gel, such as a polyvinyl alcohol gel or a gel as disclosed in EPO Patent No. 0 060 451, issued on Sep. 17, 1986 to Lattin et al. This EPO patent is incorporated by reference herein in its entirety.

A charge selective ion permeable membrane 18 is applied to the lower surface of reservoir 16. Membrane 18 forms the interface between the reservoir 16 and the skin of the patient to whom the electrode is applied. For example, if the electrode is used to deliver a negatively charged drug, membrane 18 would then be an anion permeable membrane. Examples of anionic and cationic selective membranes are described in the article "ACRYLIC ION-TRANSFER POLYMERS", by Ballestrasse et al, published in the *Journal of the Electrochemical Society*, November 1987, Vol. 134, No. 11, pp. 2745-2749. An additional appropriate anion exchange membrane would be a copolymer of styrene and divinyl benzene reacted with trimethylamine chloride to provide an anion exchange membrane. (See "Principles of Polymer Systems" by F. Rodriguez, McGraw-Hill Book Co., 1979, pgs 382-390.) These articles are incorporated herein by reference in their entirety. An additional appropriate cationic permeable material for use in conjunction with delivery of a positively charged drug would be a sulfonated styrene polymer or a sulfonated fluorocarbon polymer, e.g. Nafion TM membranes, a product of Dupont. Before applying the membrane 18 to the reservoir 16, it should be saturated with the ionic drug to be delivered. Applied to the exterior of housing 10 and membrane 18 is a release liner 20, which serves to prevent the reservoir 16 and membrane 18 from drying out during storage.

In the preferred embodiment, the provision of a sacrificial current distributing member in conjunction with an appropriately compounded drug (e.g. silver current distributing member and lithium chloride prevents the generation of ions within the electrode which have the same charge as the drug. The provision of a charge selective membrane 18 on the exterior of reservoir 16 substantially prevents migration of charged particles having a charge opposite to that of the drug into the reservoir. As such, in its preferred embodiment, the charged drug ion to be delivered will be substantially the only ionic material within the reservoir, and should be free to migrate through the reservoir 16 without any substantial competition. This provides a significant increase in efficiency of drug delivery. The membrane is also believed valuable in conjunction with iontophoresis electrodes employing inert current distributing members, in that it will at least reduce the availability of competing, mobile ions within the reservoir 16.

As noted above, the invention may be practiced in conjunction with inert current distributing members. This approach is particularly valuable in conjunction with the delivery of drugs which take the form of weak acids or weak bases. In these electrodes, hydrolysis of water is deliberately induced, with the hydrolysis product combining with the drug as compounded to produce an ionic, mobile species. For example, a weakly acidic drug D may be placed in a drug reservoir including a platinum current distributing member, which functions as the anode of the iontophoresis system. Hydrolysis of water occurs at the anode, with excess hydrogen ions combining with the drug to produce a charged species DH+ which is substantially the only charged species within the reservoir. Corresponding systems employing weakly basic drugs may also be produced. Such systems are described in more detail in the above cited patent application Ser. No. 154,566, by Untereker et al, previously incorporated by reference.

The invention of the present application is also applicable to electrodes as described in the concurrently filed application by Phipps, cited above, which employs a charge selective ion permeable membrane attached to the current distributing member. In such case, the charge selective ion permeable material applied to the current distributing member is permeable to ions having a polarity opposite to that of the drug. This membrane prevents contact between the drug ions in the reservoir and the current distributing member and prevents passage of ions formed during the oxidation or reduction of a sacrifical current distributing member into the drug reservoir.

Although disclosed in the form of a completed, disposable electrode, the present invention is also believed valuable in the context of an electrode which has a removable or reusable drug reservoir, as disclosed in the above cited EPO patent by Lattin et al. In this case, it is anticipated that the drug reservoir would be separately packaged, and include the ion selective membrane. The reservoir and membrane would be attached at a later time to the current distributing member, which might be permanently mounted to an iontophoresis device.

In conjunction with the above description, we claim:

1. An iontophoresis electrode for use on the skin of a patient, comprising:
   a conductive, current distributing member;
   means for electrically coupling said current distributing member to a source of electrical current;
   drug reservoir means electrically coupled to said current distributing member for containing an ionic or ionizable drug to be delivered and being permeable to said drug; and
   charge selective material constructed and arranged to provide a skin contacting interface in combination with the reservoir means such that the material is located between and separates the reservoir means and the skin in use of the electrode, the charge selective material being selective for ions having the same charge as said drug when ionized.

2. A method of transdermally delivering an ionic drug, comprising:
   selecting an iontophoresis electrode containing an ionic or ionizable drug, said electrode including drug reservoir means for containing said ionic drug and including a charge selective membrane fabricated of a material permeable to ions having the same charge as said drug and positioned with respect to said drug reservoir means as to provide a skin contacting interface between it and the skin of a patient to be contacted;
   applying said electrode to the skin of a patient such that said membrane is located between and separates said reservoir and said skin of said patient as an interface therebetween; and
   coupling said electrode to a source of direct electrical current.

3. A method of fabricating an iontophoresis electrode, comprising the steps of:
   providing electrode structural means constructed and arranged for delivery of ions into the skin of a patient, the means including reservoir means for holding ions to be delivered, one side of which is adapted for placement against the patient's skin, the means further including a current distribution member disposed at the other side of the reservoir means;
   selecting an ionic or ionizable drug to be delivered;
   including said drug within the reservoir means from which said drug is permeable; and
   combining charge selective material with said reservoir means, said charge selective material being permeable to ions having the same charge as said drug and being combined such that said selective material is located as an interface between and separates said reservoir means and skin against which said electrode will be contacted in use.

4. A method of increasing drug delivery efficiency from an iontophoresis electrode, the electrode including a conductive current distributing member, means for electrically coupling the current distributing member to a source of electrical current and a drug reservoir means electrically coupled to the current distributing member containing a drug which is capable of dissociating into drug ions and counter ions of opposite charge and adapted to be placed in drug transmitting relation with a body surface containing cations and anions, comprising: placing a charge selective membrane intermediate the drug reservoir and the body surface, the membrane being permeable to passage of the drug ions and substantially impermeable to passage of ions present at the skin surface and which have a charge opposite to the charge of the drug ions, whereby an alternative ionic current path from the body surface to the reservoir caused by migration of one of the ions from the body surface is minimized.

5. The method of claim 4 wherein the drug comprises a drug salt which is ionizable in a aqueous fluid.

6. The method of claim 4 wherein the membrane is comprised of an ion exchange material.

7. The method of claim 6 wherein the drug ions are positively charged and ion exchange material comprises an anion exchange membrane.

8. The method of claim 6 wherein the drug ions are negatively charged and the ion exchange material comprises a cation exchange membrane.

* * * * *